United States Patent [19]
Sachse et al.

[11] Patent Number: 5,201,749
[45] Date of Patent: Apr. 13, 1993

[54] CIRCULARLY OSCILLATING SAW

[76] Inventors: Rainer E. Sachse, 917 Dacian Ave., #7, Durham, N.C. 27701; Hans Sachse, Lerchenstrasse 55, 8500 Nurnberg, Fed. Rep. of Germany

[21] Appl. No.: 754,846

[22] Filed: Sep. 4, 1991

[51] Int. Cl.[5] .......................................... A61B 10/00
[52] U.S. Cl. .................................. 606/177; 128/755; 606/82; 606/171; 606/178; 30/393
[58] Field of Search ............... 606/171, 176, 177, 178, 606/179, 82; 128/751, 755; 30/392, 393, 394

[56] References Cited

U.S. PATENT DOCUMENTS

| | | | |
|---|---|---|---|
| 3,964,163 | 6/1976 | Russo | 606/176 X |
| 3,978,862 | 9/1976 | Morrison | 606/174 |
| 4,728,319 | 3/1988 | Masch | 606/178 X |
| 4,739,742 | 4/1988 | Alexson et al. | 606/82 |
| 4,819,334 | 4/1989 | Monegn | 30/393 |
| 4,836,069 | 6/1989 | Trandinh | 606/178 X |
| 5,087,261 | 2/1992 | Ryd et al. | 606/82 |

*Primary Examiner*—Edgar S. Burr
*Assistant Examiner*—Christopher A. Bennett
*Attorney, Agent, or Firm*—Keil & Weinkauf

[57] ABSTRACT

A circularly oscillating saw, used mainly in the surgical field which, while having minimal dimensions, must have a high cutting capacity with an atraumatic cool cut, without running hot itself. The saw provides a direct connection of the saw blade with an eccentric and a suitable bearing approximately in the center between the saw blade tip and the eccentric, which provides a circularly oscillating cutting. The saw allows a cut to take place not only in parallel to the saw blade but in all directions of a plane. In addition, contamination of a wound by lubricants and bearing debris is prevented because of the excellent transport of chips and coolant. Also, the saw is to easily cleaned, sterilized and repaired while the manufacturing of this precision instrument is efficient. An internal cooling protects from the saw running-hot and ensures an optimal coolant supply. Drive-side and output-side sealing devices achieve a hermetic sealing-off of the saw mechanism.

12 Claims, 1 Drawing Sheet

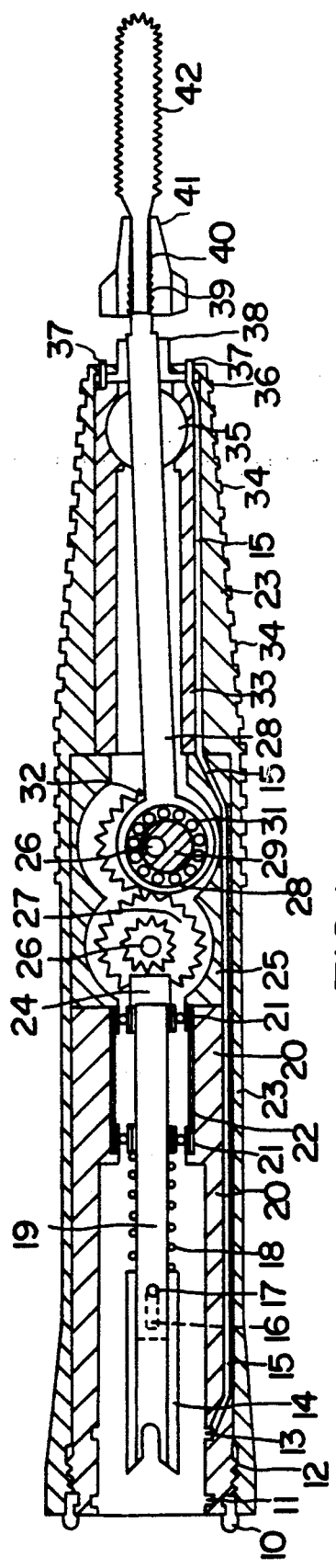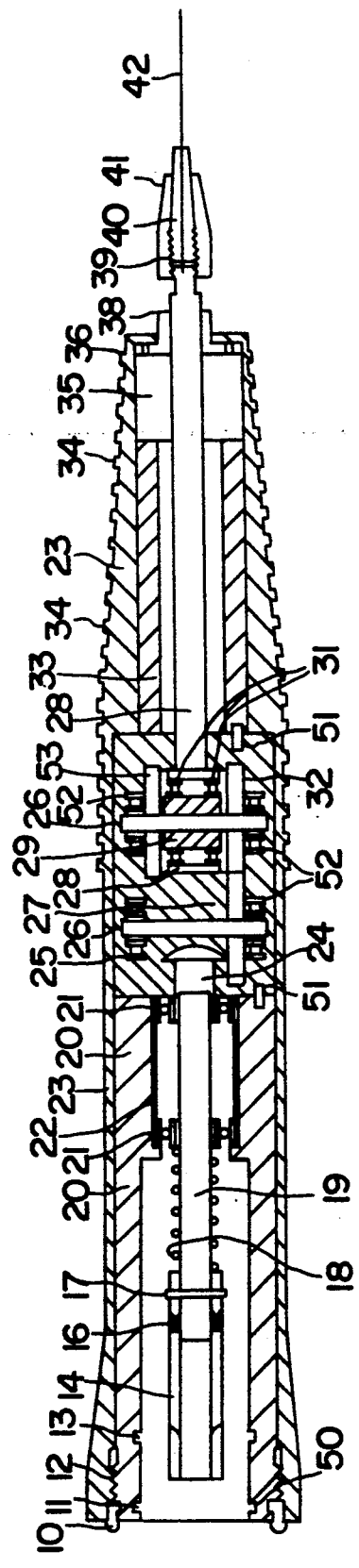

CIRCULARLY OSCILLATING SAW

The present invention relates to a circularly oscillating saw in a slender gear casing which was principally conceived for surgical purposes, particularly the cutting of bone, and has the characteristics herein described.

Instrument holders equipped with a motor drive are quite common in the field of dental medicine and surgery and are normally equipped with rotating drills or cutters. Since these dental instrument holders have a slender design, they fit well into the hand and can be used in areas that are difficult to access. However, only relatively wide cuts can be made by means of cutters. In contrast, by means of circular saw blades, which are used as an alternative, extremely thin cuts can be made; however, because of the size of the blades, these cannot be used at sites that are difficult to access. In addition, because of the geometry of the blade a certain minimum relationship exists between the depth and the length of the cut. In addition, here, just as in the case of the cutters, there is always the danger that the instrument may "run" out of the cut and grip tissue and be wound up, which is connected with extreme trauma to the tissue.

For surgical purposes, piercing saws are known in which a gear is arranged in an instrument holder which changes a rotating motion into an oscillating motion by means of which a saw blade holder is driven (U.S. Pat. No. 36 42 002, German Patent Document DE-PS 2400696, German Patent Document DE-GM 76 07 384, German Patent Document 35 00 445, German Patent Document 24 00 508, European Patent Document EP 0 125 101 B1, German Patent Document 27 49 875). While the precision is high, instrument holders of this type must be constructed to be very compact and small in order to be able to work in areas that are difficult to access; on the other hand, they must be easily disassembled, even by helpers, for the purpose of cleaning and care. However, the above-mentioned prior art saws do not meet these requirements. German Patent Document DE 3500445 meets some requirements but is very limited with respect to being disassembled. In addition, for surgical purposes, a saw must have a high cutting capacity with a cool cut by means of a good transport of chips and coolant supply. In the case of the saw mentioned in the German Patent Document DE 35 00 445, this is also not so. In addition, in the case of regular piercing saws, a cut is possible only vertically with respect to the axis of the saw blade. An improved transport of chips and a better coolant circulation in the sawing gap and a resulting high cutting capacity exists in the case of pendulum piercing saws, as they are known, for example, from the European Patent Document EP 0 125 101 B1 or the German Patent Document DE 24 00 508. However, because of their size, the former cannot be used at points which are difficult to access although a very good cutting action can be expected. However, in the case of both saws, on the one hand, the pendulum bearing is not protected from contamination and, on the other hand, cytotoxic lubricant or parts rubbed off from the bearing may enter the wound. In addition, because of the selected length relationships between the eccentric and the pendulum slide bearing as well as between the pendulum slide bearing and the saw blade tip in the case of the saw according to the German Patent Document DE 24 00 508, a cut at the tip in the manner of a piercing or the sawing with saw blades bent over the edge, as in the case of conventional piercing saws, is not possible.

In the case of all known saws, the cooling problem is also not solved, or is solved only by means of external hoses which impairs the handling of the saw; and a slipping of the nozzle often leads to an insufficient coolant supply with a resulting dying of the bone; and a hygienic cleaning is made much more difficult. In addition, running-hot of the saw cannot be prevented by external cooling. In addition, in the case of saws with a drive that can be fitted on (micromotor), there is always the risk that, because of the vibrations, the drive may turn on the saw which can very easily damage the connecting cable.

It is an object of the invention to further develop a saw of the above-mentioned type in such a manner that it permits a good cutting action in all directions of the plane of the saw blade, also by means of bent or arbitrarily shaped saw blades;

an excellent sealing of the movable parts and the bearings, an adequate internal cooling for the secure supply and distribution of coolant as well as a protection against a running-hot of the saw, an easy and fast separability for purposes of care and repair, the capacity to be cleaned and sterilized easily and efficiently, protection against a rotating of the drive on the saw, a manufacturing of a very compact construction at reasonable cost exist at the same time.

In the case of a saw of the initially mentioned type, these objects are achieved by a saw of the following characteristics:

A circularly oscillating saw in a slender gear casing, having an eccentric moved by way of a gear and directly driving a saw blade holder which is also housed in the housing, is guided in a pendulum slide bearing on the output side, and on its end, has a holding device for an easily exchangeable saw blade, characterized in that the gear casing is made of two or more parts at least in the section of the eccentric, the parts being connectable to one another by means of fitting or screwing, the gear casing is surrounded by a holding sleeve in a tightly fitting manner which holds the gear casing parts in their positions, a rubber-elastic protective sealing device is disposed between the holding sleeve and the gear casing on the output side, the saw is provided with an internally guided cooling device which is inserted in a groove milled into the gear casing and which is connected with spray nozzles integrated in the holding sleeve, the saw blade holder has a rectangular cross-section in the area of the pendulum slide bearing;

the distance from the eccentric to the pendulum slide bearing and the distance from the pendulum slide bearing to the saw blade tip are approximately identical, the saw is secured against rotation on the (standardized) driving element by means of a stop in the holding groove of the flange part.

The housing of the gear casing, which comprises the operating units of the flange part, the gear half-shells as well as the pendulum slide bearing holding device, in the holding sleeve ensures a very simply demounting by means of the opening up of only one screwed connection. As a result, sealing devices are fixed at the same time on the drive side and the output side, and thus a hermetic sealing-off of the saw is achieved, whereby contaminations of the wounds as well as of the sensitive bearings are avoided. Because of the circular oscillation of the saw blade as well as its edging with teeth, also on the front and back side, the saw can provide a thin cut in all directions of the saw blade plane, in which case a cutting performance is achieved with an optimal transport of chips and coolant that is considerably improved in comparison to the conventional piercing saws. Because of the selected length conditions, cutting in this case may also take place at an angle with respect to the axis of the saw by means of saw blades bent over the edge which is very advantageous at points that are difficult to access and, up to now, has also not been possible in the case of any other saw.

In addition, by means of the selection of a rectangular or square cross-section of the saw blade holder in the area of the pendulum slide bearing, the guiding operation of the saw blade can be improved, and rotational forces acting onto the eccentric bearing can be prevented when the chuck is opened up or tightened. The drive-side sealing device, in addition to the hermetic sealing-off of the saw, causes a damping of the residual oscillations, which still exist despite the counter-eccentric, as well as the rotation of the drive on the fastened saw. However, this function is mainly also taken over by a stop mounted in the holding groove or, as an alternative, an axial bore, into which a corresponding pin of the drive engages. As an important operational improvement, the saw also contains an internally guided water cooling system which cools not only the saw blade by way of several nozzles but also the saw itself. In this case, the cooling water is fed by means of the drive with a standardized coolant feeding system from the inside, or from the outside by means of a small hose.

By means of the selected construction form, the desired operational characteristics can be achieved in a manner which is optimal with respect to manufacturing technology, can easily be automated and saves labor.

A preferred embodiment is shown in FIGS. 1 and 2 and will be explained in detail in the following.

FIG. 1 is a lateral view of the saw which is longitudinally opened up in the center; and FIG. 2 is a lateral view of the saw in the same operating condition, but rotated by 90°.

The shown saw is disposed on a rotationally symmetrical holding sleeve 23 which tapers on the output side and is provided with gripping rings 34. By means of this holding sleeve, the parts of the gear casing (that is, the flange part 20, the two gear half shells 25 and the pendulum slide bearing 33) are held together by means of a single thread 12, in which case, the mentioned parts are secured against rotating with respect to one another by means of guide pins 51. Between the holding sleeve 23 and the pendulum slide bearing holding device 22 or the flange part 20, the drive-side and output-side rubber-elastic sealing elements 10 and 38 are held. The drive, which conventionally takes place by means of a micromotor or a bendable shaft with a standardized lengthening, by way of which the coolant is also fed axially, by means of a pin, engages in the driving device 14 which, in turn, moves the drive shaft 19 by way of an oblong hole 16 and a mandrel 17. By means of a spring 18, the driving device 14 is, in this case, pressed onto the journal of the drive. At the same time, the saw is protected from sliding off by means of a protection device against pull-off (a small detent pawl) which is standardized on the drive side and which engages in the holding groove 11. A rotation on the drive is prevented by, in addition to the sealing device 10, mainly a stop 50 situated on the holding groove 11.

In this case, the drive shaft 19 is held by two bearings 21, the distance of which is secured by a spacing sleeve 22, and has a bevel gear 24 on the output-side end. This bevel gear drives the first gear wheel 27, and this gear wheel, in turn, drives the second gear wheel 32 on which an eccentric 29 as well as a counter-eccentric 53 are situated. These gear wheels, by means of their shafts 26, run in bearings 52 which are worked into the gear half shells 25 (slide or roller bearings). By way of one or several eccentric bearings 31, the saw blade holder is then moved which, on the output side, is guided by means of a pendulum slide bearing 35. This cylindrical bearing, which is typically made of sintered metal or PTFE, in turn, is held by the pendulum slide bearing holding device 33 and is laterally held by the holding sleeve 23. The saw blade holder 28 then leaves the holding sleeve 23 while it is surrounded by the sealing device 38 before it ends in the chuck 40. In it, the saw blade 42, which may be fitted with teeth possibly on all sides, can be fastened without the aid of a tool by means of a butterfly-nut-type screw 41 which moves on a thread 39 of the chuck 40. In order to permit a secure cooling of the saw blade without any external hoses, a thin cooling line 15 is situated in a milled groove of the gear casing 20, 25 and 33 which receives its water by way of a ring-shaped groove 13 of the flange part 20 and, by way of a groove 36 of the pendulum slide bearing holding device, delivers it through the sealing device 38 which is perforated in this area, to several nozzles 37 integrated in the holding sleeve 23.

Because of the circularly oscillating movement of the saw blade 42 carried out by means of this saw, this saw blade may have not only an oblong but any arbitrary shape (also bent over the edge). Instead of the saw blade 42, files may also be used advantageously.

LIST OF REFERENCE NUMBERS

10: drive-side sealing device
11: holding groove
12: thread
13: groove for cooling water
14: driving device
15: cooling line
16: oblong hole in the driving device
17: mandrel in the drive shaft
18: pressure spring
19: drive shaft
20: flange part
21: drive shaft bearing
22: drive shaft bearing spacing sleeve
23: holding sleeve
24: bevel gear
25: gear half shells
26: gear wheels shafts
27: gear wheel 1
28: saw blade holder
29: eccentric
31: eccentric bearing
32: gear wheel 2
33: pendulum slide bearing holding device
34: gripping rings
35: pendulum slide bearing
36: groove for cooling water, output side
37: cooling water nozzles
38: output-side sealing device 39: chuck thread
40: chuck
41: chut nut
42: saw blade
43: stop in the holding groove
51: guide pin
52: gear wheel bearing
53: counter eccentric

We claim:

1. A circular oscillating saw comprising:
   a slender gear casing having an output side, a flange section opposite to said output side, a longitudinal groove milled into said casing, and a holding groove in said flange section;
   an eccentric disposed within said casing;
   a gear disposed in said casing for driving said eccentric;
   an exchangeable saw blade;
   a saw blade holder directly driven by said eccentric and having a holding device disposed at an end thereof for easily exchanging said saw blade, said saw blade holder also being disposed within said gear casing;
   a pendulum slide bearing disposed about said saw blade holder for guiding said saw blade holder through said output side;
   said gear casing having at least two parts at least in the area of said eccentric, and fitting means for connecting said at least two parts;
   a holding sleeve surrounding said gear casing to provide means for holding said at least two parts in said gear casing in the proper positions;
   said holding sleeve having spray nozzles integrally formed therein in the area of said holding sleeve which surrounds said output side of said gear casing;
   an elastic protective sealing device disposed between said holding sleeve and said output side of said gear casing;
   an internally guided cooling device inserted into said longitudinal groove of said gear casing and being connected to said spray nozzles in said holding sleeve;
   a driving element for driving said gear; and
   a stop for preventing rotation of said saw, said stop being received in said holding groove.

2. A saw as defined in claim 1, wherein an elastic protective sealing device is disposed on the drive side.

3. A saw as defined in claim 1, wherein the saw blade holder has a square cross-section in the area of the pendulum slide bearing.

4. A saw as defined in claim 1, wherein the saw blade holder has a round cross-section in the area of the pendulum slide bearing.

5. A saw as defined in claim 1, wherein the gear casing parts (flange part, gear half-shells, pendulum slide bearing holding device) are pushed into the holding sleeve as loose parts and, by means of a single thread, can be fixed securely and firmly on an end of the flange part.

6. A saw as defined in claim 1, wherein the holding sleeve reaches only to the transition from the gear half-shells to the flange part and is directly screwed together with the flange part by means of a single thread so that the gear half-shells and the pendulum slide bearing holding device are fixed.

7. A saw as defined in claim 1, wherein the distances between the eccentric and the pendulum slide bearing as well as between the pendulum slide bearing and the tip of the saw blade are different.

8. A saw as defined in claim 1, wherein the saw blade holder is guided by way of two eccentrics.

9. A saw as defined in claim 1, wherein the cooling system is external.

10. A saw as defined in claim 1, wherein an axial bore is situated in the flange part and reaches over an axial pin of the drive in order to protect against rotation.

11. A saw as defined in claim 1, wherein a bore is disposed in the holding sleeve on the drive side in which a hose projection is inserted for the cooling fluid, this bore being disposed at the same level as a groove in the gear casing which is surrounded by two sealing devices and by which the internal cooling line is fed.

12. A saw as defined in claim 1, wherein an the saw blade holder has a rectangular cross-section in the area of the pendulum slide bearing.

* * * * *

UNITED STATES PATENT AND TRADEMARK OFFICE
CERTIFICATE OF CORRECTION

PATENT NO. : 5,201,749

DATED : April 13, 1993

INVENTOR(S) : SACHSE et al.

It is certified that error appears in the above-identified patent and that said Letters Patent is hereby corrected as shown below:

IN THE CLAIMS

Claim 11, line 2, the third word of the line is illegible and should read --sleeve--.

Signed and Sealed this

Nineteenth Day of April, 1994

Attest:

BRUCE LEHMAN

*Attesting Officer*   *Commissioner of Patents and Trademarks*